(12) United States Patent
Leffel

(10) Patent No.: US 9,067,038 B2
(45) Date of Patent: Jun. 30, 2015

(54) VALVE SYSTEM FOR USE WITH A FLEXIBLE GAS SUPPLY TUBE EXTENDING TO A PATIENT

(76) Inventor: William A. Leffel, Troy, OH (US)

( * ) Notice: Subject to any disclaimer, the term of this patent is extended or adjusted under 35 U.S.C. 154(b) by 1042 days.

(21) Appl. No.: 12/584,080

(22) Filed: Aug. 31, 2009

(65) Prior Publication Data
US 2011/0048423 A1  Mar. 3, 2011

(51) Int. Cl.
| | |
|---|---|
| A62B 9/02 | (2006.01) |
| E21B 33/06 | (2006.01) |
| A61M 16/20 | (2006.01) |
| F16K 1/30 | (2006.01) |
| F16K 3/26 | (2006.01) |

(52) U.S. Cl.
CPC ....... *A61M 16/20* (2013.01); *A61M 2202/0208* (2013.01); *A61M 2205/3334* (2013.01); *A62B 9/02* (2013.01); *F16K 1/307* (2013.01); *F16K 3/26* (2013.01); *F16K 3/265* (2013.01); *A61M 16/201* (2014.02)

(58) Field of Classification Search
USPC ..................................................... 128/205.24
See application file for complete search history.

(56) References Cited

U.S. PATENT DOCUMENTS

| | | | | |
|---|---|---|---|---|
| 3,280,844 | A * | 10/1966 | Frank ........................ | 137/625.38 |
| 4,249,528 | A * | 2/1981 | Mathes ..................... | 128/205.13 |
| 4,350,647 | A * | 9/1982 | de la Cruz ................. | 261/65 |
| 4,362,052 | A * | 12/1982 | Heath et al. ................ | 73/114.42 |
| 4,467,796 | A * | 8/1984 | Beagley .................... | 128/202.13 |
| 5,038,774 | A * | 8/1991 | Chabert .................... | 128/205.24 |
| 5,280,780 | A | 1/1994 | Abel | |
| 5,336,174 | A * | 8/1994 | Daoud et al. .................... | 604/30 |
| 5,437,268 | A * | 8/1995 | Preece ...................... | 128/205.24 |
| 5,845,637 | A * | 12/1998 | Knott ....................... | 128/207.12 |
| 6,039,302 | A * | 3/2000 | Cote et al. .................. | 251/149.1 |
| 6,189,532 | B1 * | 2/2001 | Hely et al. ............... | 128/205.24 |
| 6,772,754 | B1 * | 8/2004 | Mendenhall ............. | 128/200.14 |
| 6,848,722 | B2 * | 2/2005 | Jeory ........................... | 285/305 |
| 2003/0127099 | A1 * | 7/2003 | Meneuvrier et al. ..... | 128/204.26 |

\* cited by examiner

*Primary Examiner* — Tan-Uyen (Jackie) T Ho
*Assistant Examiner* — Eric Bryant
(74) *Attorney, Agent, or Firm* — Hahn, Loeser & Parks, LLP; Rex W. Miller, II

(57) ABSTRACT

Low pressure oxygen or other breathable gas is supplied from a tank or other source to a patient or other person through a flexible plastic tube, and a safety valve system is connected between the source and the tube. The valve system includes a valve member having a tubular outlet portion and supported for axial movement within a valve body having an inlet connected to the gas source. Fluid passages are formed within the valve member and valve body, and the valve member shifts axially to an open position in response to connecting the flexible tube to the tubular outlet portion of the valve member. The valve member shifts to a closed position in response to removing the tube from the tubular outlet portion, and the supply gas holds the valve member in the closed position.

20 Claims, 2 Drawing Sheets

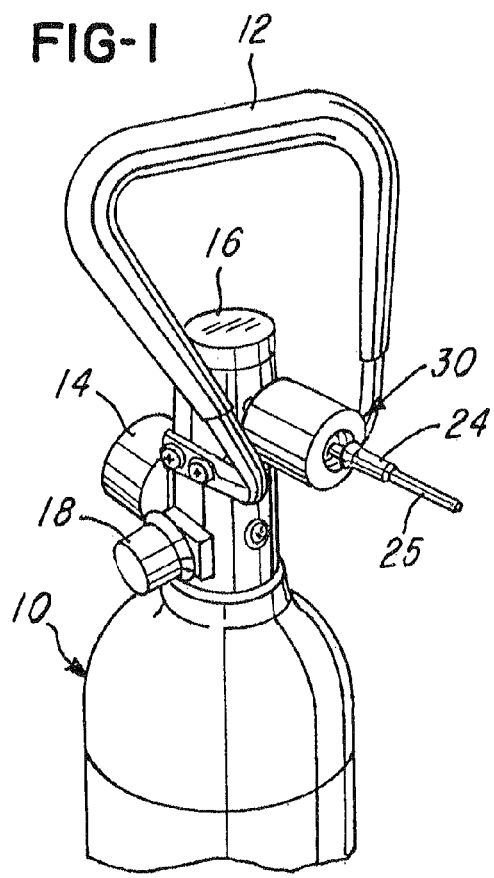
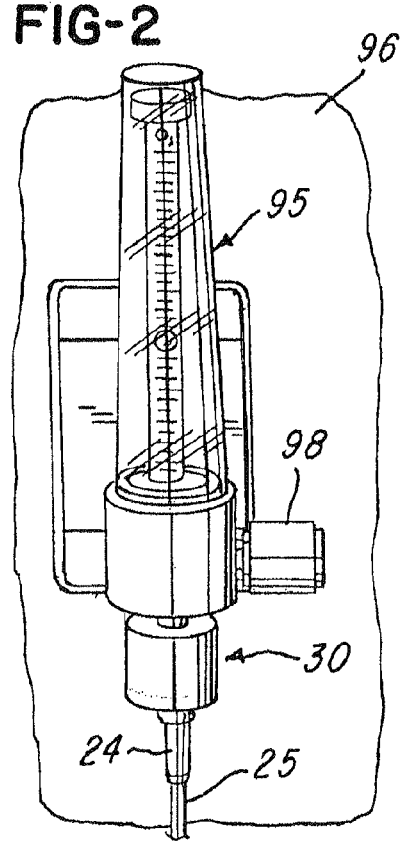
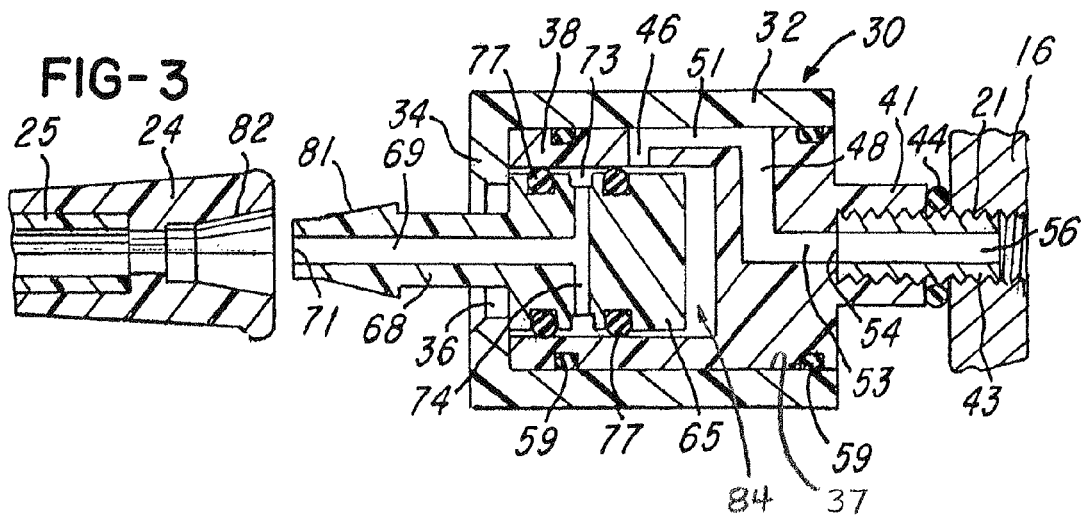

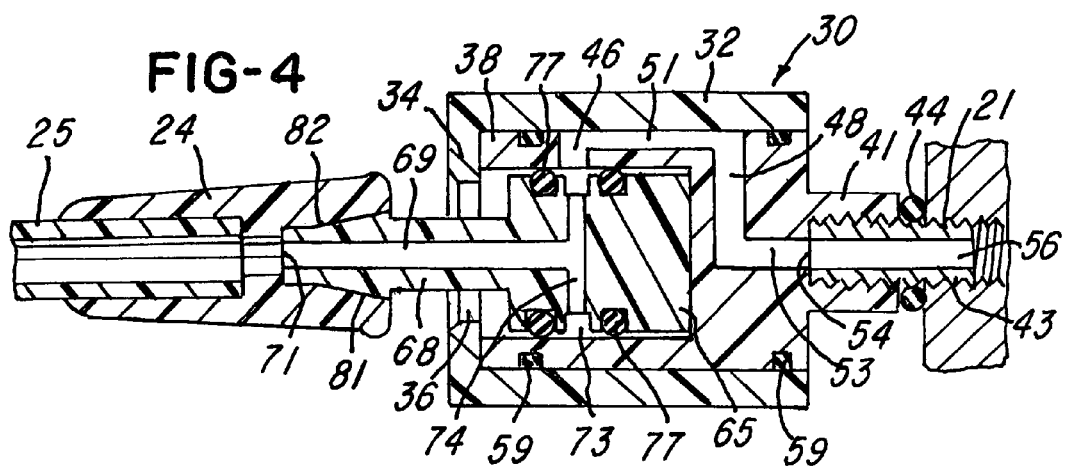
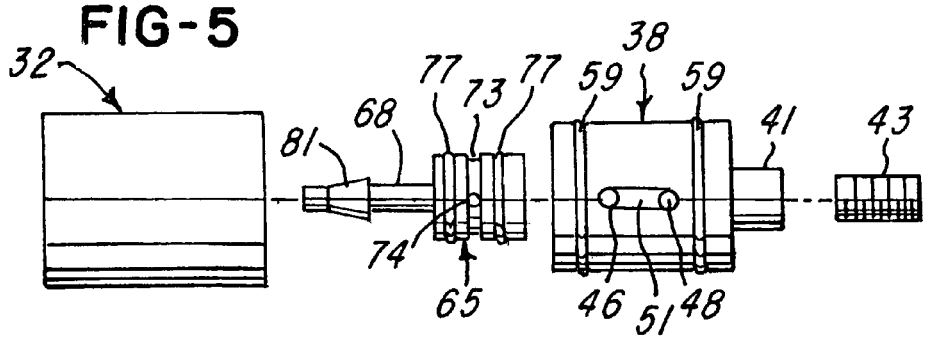

VALVE SYSTEM FOR USE WITH A FLEXIBLE GAS SUPPLY TUBE EXTENDING TO A PATIENT

BACKGROUND OF THE INVENTION

In the supply of low pressure oxygen or other breathable therapeutic gas from a portable supply tank or from a fixed gas supply source in a hospital, a clear flexible plastic tube is commonly used to connect the oxygen supply tank or source to a face mask or nosepiece or tent for a patient or other person requiring the gas. Frequently, it is necessary for the patient to disconnect the flexible gas supply tube from the supply tank or gas source so that the patient may move away from the supply tank or source. This requires that the patient first shut off a valve on the supply tank or supply source. However, it has been found that all too frequently, the valve is not completely shut off, and low pressure oxygen or gas continues to leak from the source through the valve and into the room or space surrounding the gas supply. If the gas leak is not discovered and continues, the escaping gas can be dangerous and/or create an unnecessary expense.

One form of valve for use in a low pressure gas delivery system is disclosed in U.S. Pat. No. 6,189,532. This valve permits the patient to vent to atmosphere in the event gas supply diminishes or terminates. Another form of valve system is disclosed in U.S. Pat. No. 5,280,780 and is used in an oxygen delivery tube extending to a patient to prevent oxygen from being wasted during exhalation by the patient. Other forms of control valves are also used in ventilation gas apparatus or systems.

SUMMARY OF THE INVENTION

The present invention is directed to an improved valve system for use between a low pressure source of oxygen or other gas and a flexible tube for dispensing the gas through the tube to a face mask or nosepiece or tent for a patient. In accordance with one embodiment of the valve system, a valve body defines a gas inlet port and gas passages, and a valve member is supported within the valve body for movement on an axis. The valve member includes an axially projecting tubular portion and defines a fluid passage with an outlet port in the tubular portion. Annular sliding fluid seals extend between the valve body and the valve member which moves axially to an open position connecting the fluid passages in response to an axial pushing force produced when the flexible tube is connected to the tubular portion of the valve member. The valve member moves to a closed position blocking the fluid passages within the valve body from the fluid passages within the valve member in response to an axial pulling force on the tubular portion of the valve member when the flexible tube is removed from the tubular portion of the valve member. Thus the valve system of the invention prevents gas from escaping from the gas supply tank or source when the flexible tube is removed from the tank or source.

BRIEF DESCRIPTION OF THE DRAWINGS

FIG. 1 is a fragmentary perspective view of a conventional portable oxygen supply tank and supporting a safety valve system constructed in accordance with the invention;

FIG. 2 is an elevational view of an oxygen supply fixture commonly mounted on a wall of a hospital room and supporting a valve system constructed in accordance with the invention;

FIG. 3 is an enlarged axial section of the valve system shown in FIGS. 1 & 2 and with the valve system in its closed position prior to receiving a flexible gas supply tube;

FIG. 4 is an enlarged axial section of the valve system shown in FIG. 3 and in its open position after connecting a flexible tube to the valve system; and FIG. 5 is an exploded plan view of the components used in the valve system shown in section in FIGS. 3 & 4.

DESCRIPTION OF THE PREFERRED EMBODIMENT

FIG. 1 illustrates a conventional portable tank 10 which is filled with a compressed gas such as oxygen and which includes a handle 12, a gauge 14 and a pressure regulator 16 with an on-off valve having a control knob 18. The regulator 16 has an internally threaded outlet port 21 (FIG. 3) through which low pressure gas or oxygen is dispensed. Usually, the threaded outlet 21 receives a tubular nipple or fitting which receives a resilient molded plastic sleeve 24 mounted on and sealed to an end portion of a flexible clear plastic tube 25. The tube 25 extends to a patient or other person requiring the therapeutic gas or oxygen, and the opposite end portion of the tube 25 is connected to a face mask or nosepiece attached to the person or to a tent which covers a patient's head.

In accordance with the present invention, a safety valve unit or system is supported by the regulator 16 of the pressurized gas or oxygen tank 10 and includes a cylindrical housing or outer valve body 32 having an end wall 34 with a circular opening 36. The outer valve body 32 has a cylindrical bore 37 which receives a cylindrical inner valve body 38 having an internally threaded tubular gas inlet portion 41. An externally threaded tubular nipple 43 is partially threaded into the inlet portion 41 and partially threaded into the outlet port 21 of the regulator 16 so that the valve system 30 is supported in a cantilevered manner by the regulator 16 on the tank 10, as shown in FIG. 1. A resilient O-ring 44 forms a fluid-tight seal between the regulator 16 and the inlet portion 41 of the inner valve body 38.

The inner valve body 38 also has two axially spaced and radially extending holes or passages 46 and 48 (FIGS. 3 & 5) which are connected by an axially extending groove or passage 51. The passage 48 connects with an axially extending center passage 53 which defines an inlet port 54 for the valve body 38 and connects with an axial aligned center passage 56 within the tubular nipple 43. The inner valve body 38 has a pair of axially spaced circumferential grooves which receives a pair of resilient O-rings 59 to form corresponding fluid-tight seals between the outer valve body 32 and the inner valve body 38.

A spool-like valve member 65 (FIG. 3) is supported within the inner valve body 38 for axial movement and includes a tubular portion 68 which projects axially through the opening 36 within the outer valve body 32 and has an axially extending center passage 69 with an outlet port 71. The valve member 65 also has a circumferentially extending groove 73 which is connected by a diametrically extending passage 74 to the center passage 69 within the valve member. The valve member 65 has a pair of axially spaced circumferential grooves which receives a corresponding pair of resilient O-rings 77 to form a sliding fluid-tight seal between the valve member 65 and the inner valve body 38. The tubular outlet portion 68 of the valve member 65 has a tapered or frusto-conical surface 81 which is adapted to receive a substantially mating tapered surface 82 within the resilient plastic sleeve 24.

As shown in FIG. 3, the valve unit or system 30 is shown in its closed position with the valve member 65 engaging the end wall 34 of the outer valve body 32. In this closed position, low pressure gas within the passages 53 and 56 is directed through the passages 48, 51 and 46 and to a valve chamber 84 so that the low pressure gas holds the valve member in the closed position where the O-ring seals 77 prevent any gas pressure from entering the groove 73 and passages 74 and 69.

As shown in FIGS. 3 & 4, when it is desired to connect the flexible plastic tube 25 to the valve system 30, the resilient sleeve 24 on the end of the tube 25 is pressed axially onto the tubular portion 68 of the valve member 65 until the mating surfaces 81 and 82 form a fluid-tight friction seal. The axial force required to press the sleeve 24 onto the tubular portion 68 is sufficient to move or shift the valve member 65 to an open position, as shown in FIG. 4. In the open position, low pressure gas flows through the passages 56, 53, 48, 51, 46 and into the annular groove 73 and through the passages 74 and 69 and outlet port 71 into the flexible tube 25. When it is desired to remove the tube 25 from the valve system 30 so that the tube 25 may be carried by the patient or person away from the gas supply, the sleeve 24 is gripped and pulled axially away from the valve system. The frictional grip of the sleeve 24 on the surface 81 of the valve member 65 is sufficient to pull or shift the valve member 65 from its open position (FIG. 4) back to its closed position (FIG. 3). In the closed position, the low pressure gas is blocked by the valve member 65 from entering the groove 73 and passages 74 and 69. As a result, low pressure gas is prevented from exiting the outlet port 71 of the valve system.

The actual size of the components of the valve system 30 is shown in FIG. 5, and all of the components are formed from rigid plastics material, with the exception of the rubber or resilient O-rings 59 and 77. As shown in FIG. 2, the valve system 30 may also be used with a fixed low pressure gas or oxygen dispensing fixture 95 that is commonly mounted on a wall surface 96 of a hospital room above a hospital bed. The fixture 95 has a control valve operated by a knob 98 for turning the low pressure oxygen supply on and off. When the valve is not completely closed, the valve unit or system stops the escape of gas in the event the tube 25 is removed.

From the drawings and the above description, it is apparent a valve unit or system 30 constructed and used in accordance with the invention provides desirable features and advantages. As a primary advantage, if the control valve within the regulator 16 or within the fixture 95 is inadvertently not completely shut off by rotating and tightening the knob 18 or 98, the valve system 30 assures that the flow of low pressure gas is completely shut off when the flexible tube 25 and coupling sleeve 24 is removed from the valve system. As a result, none of the low pressure gas or oxygen continues to leak or seep into the surrounding room or atmosphere. This not only improves safety in the use of the gas or oxygen supply, but also conserves the supply of gas or oxygen by preventing the continuing escape of the gas. These advantages are especially important with a portable gas or oxygen tank as shown in FIG. 1 since it is not uncommon for the control valve within the regulator 16 to be completely shut off by the user before the flexible tube 25 is disconnected so that the user may move or walk to a different location without carrying the gas supply tank 10.

While the form of valve system herein described and its use constitutes a preferred embodiment of the invention, it is to be understood that the invention is not limited to this precise form of valve system, and that changes may be made therein without departing from the scope and spirit of the invention as defined in the appended claims. For example, the outer valve body 32 and inner valve body 38 may be made as one piece. The passages 46, 48 and 51 could then be molded or drilled, after which end portions of the passages would be plugged.

What is claimed is:

1. A safety valve system connecting a source of low pressure therapeutic gas to a flexible tube for dispensing the low pressure therapeutic gas through said flexible tube to a patient or other person, said safety valve system comprising:
a valve body of rigid material and defining a gas inlet and a gas passage,
a valve member of rigid material and supported within said valve body for linear movement on an axis,
said valve member including an axially projecting tubular portion and defining a gas passage with an outlet port in said axially projecting tubular portion,
said flexible tube having an end portion supporting a resilient coupling sleeve releasably connected by friction to said axially projecting tubular portion of said valve member,
axially spaced annular gas seals carried by said valve member and engaging said valve body,
said valve member movable axially within said valve body to an open position connecting said gas passage within said valve member between said axially spaced annular gas seals to said gas passage within said valve body in response to pushing said resilient coupling sleeve onto said axially projecting tubular portion of said valve member, and
said valve member movable to a closed position where said gas passage within said valve member is blocked by said axially spaced annular gas seals from said gas passage within said valve body in response to pulling said resilient coupling sleeve from said axially projecting tubular portion of said valve member with a force overcoming said friction to remove said resilient coupling sleeve and said flexible tube from said axially projecting tubular portion of said valve member.

2. The safety valve system as defined in claim 1 wherein said valve body comprises an outer valve body surrounding an inner valve body, and said outer valve body has an annular end wall surrounding said tubular portion of said valve member and forming a stop against axial movement of said valve member to said closed position.

3. The safety valve system as defined in claim 2 and including axially spaced resilient annular seals between said inner valve body and said outer valve body.

4. The safety valve system as defined in claim 1 wherein said projecting tubular portion of said valve member includes a tapered outer surface forming a gas-tight seal with a tapered inner surface within said resilient coupling sleeve on said end portion of said flexible tube.

5. The safety valve system as defined in claim 1 in combination with a portable tank of pressurized gas, and said valve body is connected to and supported by said tank.

6. The safety valve system as defined in claim 1 in combination with a gas supply fixture adapted to be mounted on a wall of a building, and said valve body is connected to and supported by said fixture.

7. The safety valve system as defined in claim 1 wherein said valve member has a cylindrical outer surface with axially spaced circumferential grooves, said axially spaced annular gas seals comprise resilient sealing rings supported within said grooves, and said gas passage within said valve member extends from between said grooves to said outlet port in said tubular portion.

8. The safety valve system as defined in claim 1 wherein said valve body includes a tubular inlet portion adapted to be threadably connected to said source of low pressure therapeutic gas.

9. The safety valve system as defined in claim 8 wherein said tubular inlet portion of said valve body has internal threads, and an externally threaded nipple extending into said inlet portion and adapted to extend into an internally threaded outlet portion of said source of low pressure therapeutic gas.

10. A valve system adapted to fluidly engage an associated source of low pressure gas with an associated dispensing tube, said valve system comprising:
- an elongated outer valve body having
  - an end wall, and
  - an internal bore;
- a hollow elongated inner valve body at least partially located within the internal bore and engaged with the internal bore to form a fluid tight seal, said hollow elongated inner valve body having a first fluid passage therethrough;
- a valve member slidably engaged within said hollow elongated inner valve body, said valve member,
  - having an outlet port,
  - being positionable at a first position within said hollow elongated inner valve body at which first position said first fluid passage is in fluid communication with said outlet port, and
  - being positionable at a second position within said hollow elongated inner valve body at which second position,
    - a valve chamber is defined between said valve member and said hollow elongated inner valve body, and
    - said first fluid passage is in fluid communication with said valve chamber.

11. The valve system as defined in claim 10 wherein said end wall has a hole through which a tubular portion of said valve member extends and which forms a stop adapted to limit axial movement of said valve member.

12. The valve system as defined in claim 11 and including axially spaced seals between said inner valve body and said outer valve body.

13. The valve system as defined in claim 11 wherein said tubular portion of said valve member includes a tapered outer surface adapted to form a gas-tight seal with an associated tapered inner surface.

14. The valve system as defined in claim 13, wherein said fluid passage is engaged with a portable tank of pressurized gas.

15. The valve system as defined in claim 13, wherein said fluid passage is engaged with a gas supply fixture affixed to a wall of a building.

16. The valve system as defined in claim 13 wherein said valve member has
- a cylindrical outer surface with axially spaced circumferential grooves,
- resilient annular gas sealing rings supported within said axially spaced circumferential grooves, and
- a second fluid passage which extends from between said axially spaced circumferential grooves to said outlet port.

17. The valve system as defined in claim 13 wherein said first fluid passage has a tubular inlet portion adapted to be threadably connected to said associated source of low pressure gas.

18. The valve system as defined in claim 17 wherein said tubular inlet portion has internal threads threadedly engaged with an externally threaded nipple extending into said tubular inlet portion, said externally threaded nipple being adapted to extend into an internally threaded outlet portion of said associated source of low pressure gas.

19. A method of fluidly engaging a valve system between an associated source of low pressure gas and to an associated dispensing tube, said method comprising:
- providing a valve system adapted to fluidly engage an associated source of low pressure gas with an associated dispensing tube, said valve system having
  - an elongated outer valve body having
    - an end wall, and
    - an internal bore;
  - a hollow elongated inner valve body at least partially located within the internal bore and engaged with the internal bore to form a fluid tight seal, said hollow elongated inner valve body having a first fluid passage therethrough;
  - a valve member slidably engaged within said hollow elongated inner valve body, said valve member,
    - having an outlet port,
    - being positionable at a first position within said hollow elongated inner valve body at which first position said first fluid passage is in fluid communication with said outlet port, and
    - being positionable at a second position within said hollow elongated inner valve body at which second position,
      - a valve chamber is defined between said valve member and said hollow elongated inner valve body, and
      - said first fluid passage is in fluid communication with said valve chamber;
- providing a source of low pressure gas, said source of low pressure gas being either,
  - a portable tank of pressurized gas, or
  - a gas supply fixture affixed to a wall of a building;
- providing a dispensing tube;
- fluidly engaging said first fluid passage with said source of low pressure gas; and
- fluidly engaging said outlet port with said dispensing tube.

20. The valve system as defined in claim 10 wherein the hollow elongated inner valve body is secured to the elongated outer valve body such that the hollow elongated inner valve body is stationary with respect to the elongated outer valve body, and wherein the elongated inner valve body and the elongated outer valve body have an opening through which the outlet port of the valve member extends.

* * * * *